United States Patent [19]

Zang et al.

[11] Patent Number: 5,720,766
[45] Date of Patent: Feb. 24, 1998

[54] APPARATUS FOR ATTACHING SOFT TISSUE TO BONE

[75] Inventors: Kerry Zang, Paradise Valley; Jeffry Skiba, Phoenix, both of Ariz.

[73] Assignee: Orthopaedic Biosystems Limited, Inc., Scottsdale, Ariz.

[21] Appl. No.: 696,897
[22] PCT Filed: Feb. 23, 1995
[86] PCT No.: PCT/US95/02401
  § 371 Date: Oct. 21, 1996
  § 102(e) Date: Oct. 21, 1996
[87] PCT Pub. No.: WO95/22930
  PCT Pub. Date: Aug. 31, 1995
[51] Int. Cl.⁶ .................................................... A61B 17/00
[52] U.S. Cl. ........................ 606/232; 606/73; 606/104
[58] Field of Search ................... 606/232, 60, 72, 606/73, 65, 66, 67, 104; 411/511; 62/13

[56] References Cited

U.S. PATENT DOCUMENTS

| | | | |
|---|---|---|---|
| 4,738,255 | 4/1988 | Goble et al. | 606/232 |
| 4,988,351 | 1/1991 | Paulos et al. | 606/73 |
| 5,013,316 | 5/1991 | Goble et al. | 606/232 |
| 5,037,422 | 8/1991 | Hayhurst et al. | 606/232 |
| 5,102,421 | 4/1992 | Anspach, Jr. | 606/232 |
| 5,224,946 | 7/1993 | Hayhurst et al. | 606/232 |
| 5,336,240 | 8/1994 | Metzler et al. | 606/232 |
| 5,370,662 | 12/1994 | Stone et al. | 606/73 |

*Primary Examiner*—Gary Jackson
*Attorney, Agent, or Firm*—Snell & Wilmer L.L.P.

[57] ABSTRACT

An anchor for attaching soft tissue to a bone comprising a head having a central dome with a suture bore extending therethrough. The dome includes a pair of substantially flat, oppositely disposed lands configured for engagement to a driving tool for inserting the anchor into the bone. A shaft extend from the head, and includes a first series of helical threads having a first diameter, and second series of helical threads interleaved with the first series of threads. The second series of threads has a diameter substantially different than the first diameter. The anchor employs a guide wire bore extending along the length of the anchor shaft.

4 Claims, 6 Drawing Sheets

APPARATUS FOR ATTACHING SOFT TISSUE TO BONE

TECHNICAL FIELD

The present invention relates generally to apparatus for attaching soft tissue to bone, and more particularly to a bone anchor which functions as an attachment site for sutures used to retain soft tissue in intimate contact with a bone to permit reattachment of the soft tissue to the bone.

BACKGROUND ART AND TECHNICAL PROBLEM

The principal components of a skeletal system, for example a human skeletal system, include bones which comprise the framework for the body, cartilage which forms the connecting and supporting structures among the bones, and ligaments which bind the bones together. When a ligament becomes detached from a bone, for example due to an athletic or other injury, it is often desirable to reattach the ligament to the bone.

Ligaments and other soft tissue (e.g., tendons) may be reattached to a bone in a number of different ways. For example, Goble et al., U.S. Pat. No. 5,013,316, issued May 7, 1991, discloses a soft tissue anchor comprising a footing stud that includes a drill and followed by self tapping threads, wherein the footing stud is arranged for turning and tapping into a bone mass. A longitudinal hole is disposed within the footing stud and is configured to receive and retain therein a tack which includes an undersurface comprising spikes for engaging and penetrating a ligament. When the tack is urged into the bore of the footing stud, the spikes engage the soft tissue and maintain it in intimate contact with the bone.

Goble et al., U.S. Pat. No. 4,738,255, issued Apr. 19, 1989, discloses a suture anchor system that includes a drill and guide arrangement for drilling an opening into a bone mass which is outwardly flared to accommodate a suture anchor dispensed from an applicator, which suture anchor is configured to be expanded within the bone mass to secure the anchor within the undersurface of the bone. As tension is applied to the suture, the anchor remains underneath the surface of the bone.

Hayhurst et al., U.S. Pat. No. 5,037,422, issued Aug. 6, 1991, discloses a bone anchor which comprises an elongated, thimble-shaped body having slots extending lengthwise through the body and a suture receiving opening provided in the tip of the body. At least one ridge or barb extends outwardly from the exterior of the body and defines an edge which is adapted to be lodged in the wall of a bore formed in the bone mass. The tip of the anchor is configured to be inserted into a bore in the bone, such that when tension is applied to the sutures, the resilient walls of the anchor are flared outwardly, locking the anchor into the bore within the bone.

Paulos et al., U.S. Pat. No. 4,988,351, issued Jan. 29, 1991, discloses a soft tissue washer for use with a bone screw for attaching soft tissue to a bone. The washer comprises a plurality of sharp pins extending from the distal face of the washer, there being a plurality of posts interposed among the pins also extending from the distal face of the washer. The washer comprises a central bore for receiving a bone screw therewithin. As the bone screw is tightened into the bone, the sharp pins engage the soft tissue to retain the tissue in intimate contact with the bone; the posts limit the degree of penetration of the pins into the bone such that the distal face of the washer is maintained a predetermined distance from the bone surface, such that the soft tissue is maintained between the distal face of the washer and the bone.

Anspach Jr., U.S. Pat. No. 5,102,421, issued Apr. 7, 1992, discloses a suture anchor in the form of a rivet having three radially extended flanges configured for penetration into a bone. A cylindrical extension projects rearwardly from the flanges and has a suture secured thereto. A plurality of spiral grooves are formed within the flanges to facilitate turning of the ankle as it is tapped into a bone mass. The aforementioned grooves also serve to define a series of serrations therebetween, which serrations aid in preventing withdrawal of the anchor.

Other known devices attempt to dispose the suture anchor site wholly within or underneath the bone surface, such as the "Quick Anchor" bone anchor manufactured by Mitek Surgical Products, Inc. of Norwood, Mass. The Mitek Quick Anchor bone anchor is configured to be dropped within a bore of a bone mass using a collar device, functioning to retain expandable wings in a retracted position during insertion. Once the device is inserted into the bone cavity, the wings expand, much like a grappling hook, to prevent withdrawal of the device. Presently known suture anchor devices are unsatisfactory in several respects. For example, the suture attachment sites of many known devices are of sharp or otherwise irregular construction, tending to irritate adjacent tissue. Moreover, many known devices tend to migrate within the bone mass, which may result in the device becoming lodged within a joint. In addition, presently known devices require cumbersome tools and accessories for inserting the device, for example devices which require turning or screwing during insertion.

A suture anchor is thus needed which overcomes the shortcomings of the prior art.

SUMMARY OF THE INVENTION

The present invention provides a suture anchor which addresses the shortcomings associated with the prior art.

In accordance with one aspect of the present invention, a bone is provided which includes an elongated shaft having a flat head portion attached to a proximal end thereof. The head portion further comprises a rounded cap or dome which functions as a suture anchor site. During installation, the surgeon drills an elongated bore into the bone mass, and presses the shaft portion of the bone anchor into the bore. In accordance with a further aspect of the present invention, the bore includes a counterbore configured to receive the flat head portion of the anchor. The dome extending from the flat portion is suitably configured with openings through which sutures may be threaded, such that the sutures are securely anchored to the bone by the anchor device. The sutures may then be attached to soft tissue in a conventional manner.

In accordance with a further aspect of the present invention, the elongated shaft portion of the anchor device comprises a plurality of frustroconical tines which, when tension is applied to the sutures, tend to flare outwardly, locking the anchor in place and preventing outward migration of the device. Inward migration of the device is precluded by the engagement of the undersurface of the flat head portion of the device with the counterbore.

In accordance with yet a further aspect of the invention, the dome portion of the anchor device is suitably of integral construction with the head portion of the device, resulting in superior pullout strength of the device.

In accordance with yet a further aspect of the invention, the shaft portion of the anchor device comprises a plurality of lengthwise grooves extending along the length of the shaft resulting in a plurality of arcuate, spaced-apart tines extending along the length of the shaft. These grooves provide sites for bony ongrowth, further preventing axial and rotational migration of the device within the bone.

BRIEF DESCRIPTION OF THE DRAWING FIGURES

The subject invention will be hereinafter described in conjunction with the appended drawing figures, wherein like numerals designate like elements, and:

DETAILED DESCRIPTION OF PREFERRED EXEMPLARY EMBODIMENTS

Figure 1:
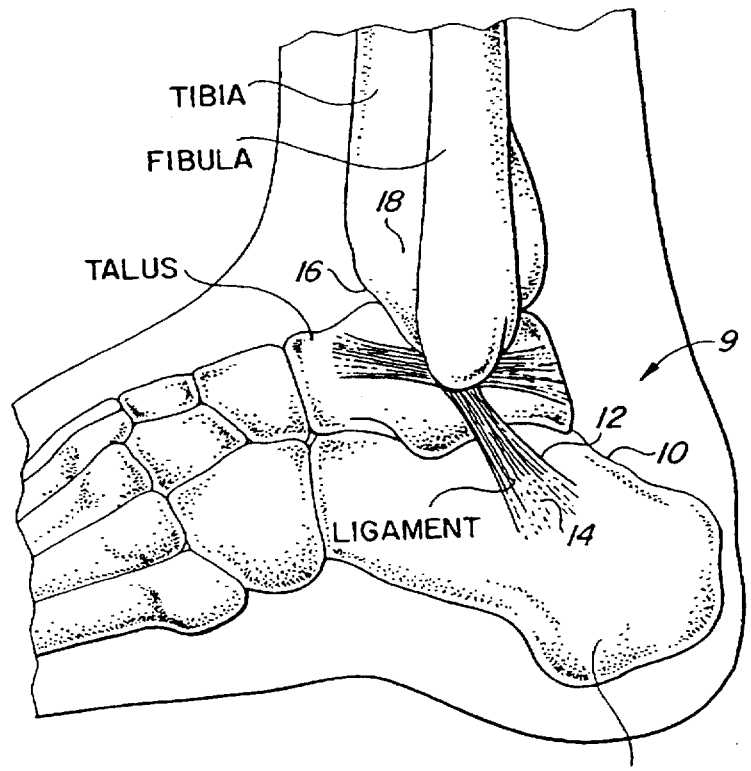
FIG. 1 is a schematic view of an anatomically normal human heel bone showing soft tissue properly attached to the bone.

Referring now to FIG. 1, a ligament 12 extends between a human tibia 16 and a human calcaneus bone (heel bone) 10 in an anatomically normal ankle joint. Ligament 12 is attached to tibia 16 at an attachment site 18, and attached to calcaneus 10 at an attachment site 14. Although attachment sites 14 and 18 appear to form an arcuate line in FIG. 1, those skilled in art will appreciate that soft tissues such as ligament 12 typically adheres to a bone over an irregular region which, for purposes of this discussion, is approximated by the arcuate attachment site shown in the Figure.

When soft tissue such as ligament 12 becomes detached from the bone, for example, as a result of an athletic injury or the like, it is often desirable to reattach the soft tissue to the bone. In this regard, it has become common practice to grasp the free (detached) end of the tissue with sutures, and to securely anchor the sutures to the bone proximate the reattachment site. If desired, the adjacent joint may be immobilized for a period of time to permit reattachment. With the soft tissue held in intimate contact with the bone, the tissue will naturally grow back into the bone surface, firmly reattaching itself to the bone in a relatively short period of time. For example, soft tissue 12 may begin reattaching itself to calcaneus 10 in a matter of twenty-one days, and will be substantially reattached to the point that the patient may walk on the ankle joint in as little as eight weeks. After approximately sixteen weeks, the reattachment process is substantially completed.

The natural physiological process whereby the soft tissue grows back into the bone occurs relatively quickly; hence, the useful life of the bone anchor device used to attach the suture to the bone proximate the reattachment site is thus on the order of sixteen weeks. However, because removal of the anchor device may require destruction of at least a portion of the reattached tissue, it is often desirable to simply permit the suture anchor to remain within the bone permanently. That being the case, it is highly desirable that the suture anchor exhibit a high pullout strength during the early stages of reattachment, and to exhibit a high resistance to migration thereafter. In addition, inasmuch as the suture anchor typically remains in situ permanently, it is desirable that the suture anchor be minimally intrusive; that is, the suture anchor advantageously comprises smooth, anatomically compatible surfaces exposed to adjacent tissue and bony structure.

Figure 2A:
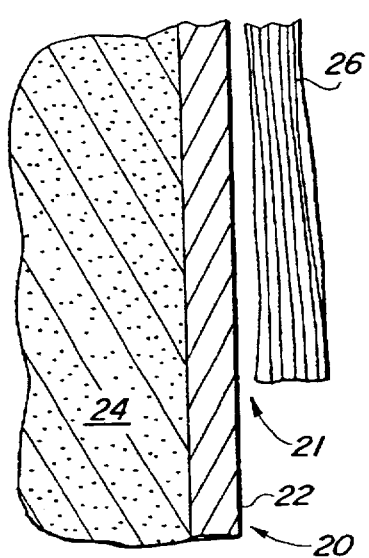
FIG. 2A is a schematic diagram of an exemplary flat bone anchor site showing soft tissue detached from the bone.
Figure 2B:
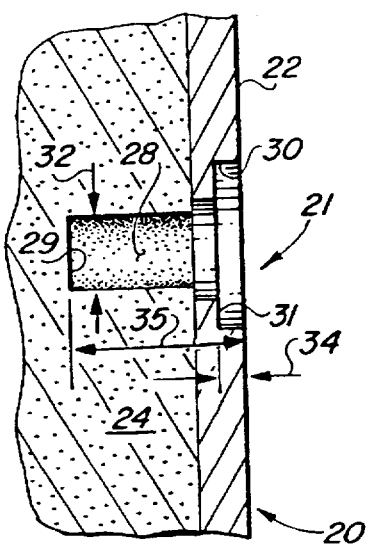
FIG. 2B is a schematic diagram of the bone anchor site of FIG. 2A shown prepared for receiving the bone anchor of the present invention.
Figure 2C:
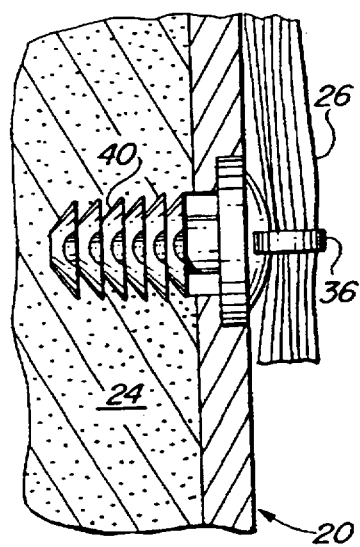
FIG. 2C shows the bone anchor site of FIGS. 2A and 2B showing the subject bone anchor in situ, maintaining the reattached soft tissue in intimate contact with the bone.

Referring now to FIGS. 2A–2C, an exemplary soft tissue reattachment site 21 suitably comprises a bone 20 (for example analogous to calcaneus 10) and soft tissue 26 (for example analogous to ligament 12) which has become detached from bone 20. Those skilled in the art will appreciate that the structure of bone tissue is generally either compact, cortical bone, i.e., the hard, dense, outside layer of bone, or spongy (also referred to herein as cancellous bone), which contains many small cavities which may be filled with marrow. Moreover, bones are also generally classified according to their shape; that is, bones are either long (as in the bones of the extremities), short (for example, bones of the wrist, ankle, and sesamoid bones), or flat (such as bones of the cranium, scapula, and ribs). In addition, certain bones, for example bones of the vertebrae, are classified as irregular.

With continued reference to FIG. 2A, bone 20 may comprise a flat bone having an outer layer 22 of compact bone enclosing an inner-region 24 of cancellous bone.

Referring now to FIG. 2B, reattachment site 21 may be suitably prepared for reattachment of soft tissue 26 (not shown in FIG. 2B for clarity), by forming a bore 28 extending through outer layer 22 and into the cancellous portion 24 of bone 20. With momentary reference to FIG. 2C, an exemplary suture anchor device 40 may then be inserted into bore 28 to maintain soft tissue 26 in intimate contact with bone 20 to permit the soft tissue to naturally reattach itself to the bone.

Figure 3:
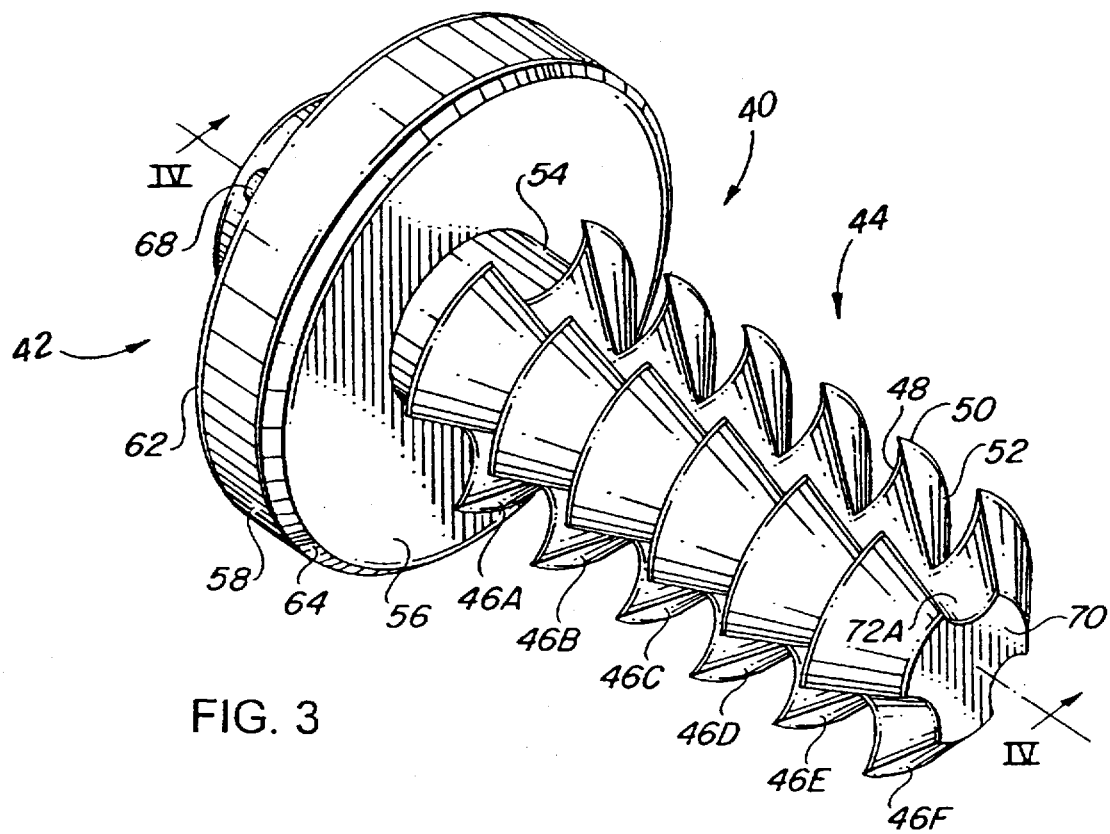
FIG. 3 is a side elevational view of an exemplary embodiment of the bone anchor device in accordance with the present invention.

Referring now to FIG. 3, suture anchor 40 suitably comprises a shaft portion 44, a head portion 42, and a neck portion 54 interposed therebetween. Neck portion 54 is suitably integral with head portion 42, and in a preferred exemplary embodiment, is substantially cylindrical in shape.

Head portion 42 suitably comprises a disc portion 43 and a dome 66 extending therefrom. Dome 66 advantageously includes one or more suture tunnels 68, as described in greater detail below in conjunction with FIGS. 5 and 6.

Disc portion 43 further comprises a substantially flat, annular, undersurface 56 and a substantially flat, annular upper surface 60 separated by a circumferential land 58. In accordance with a preferred exemplary embodiment, disc portion 43 suitably comprises a first beveled surface 62 joining land 58 and upper surface 60, and a second bevelled surface 64 joining land 58 and undersurface 56.

With continued reference to FIG. 3, shaft portion 44 suitably comprises a plurality of frustroconical tines 46A–46F. In the illustrated embodiment, shaft portion 44 suitably comprises six (6) tine segments, namely, respective segments 46A–46F. However, any suitable number of tine portions may be employed in the context of the present invention, for example in the range of one to twelve or more, depending on the particular bone mass within which the device is to be installed, and most preferably on the order of four to eight tine portions.

In accordance with a further aspect of the invention, respective tine portions 46A–46F each comprise a flat annular surface 48 disposed in a plane substantially perpendicular to the longitudinal axis of anchor 40, an angled, frustroconical portion 52, and an arcuate junction 50 defining the junction between flat portion 48 and angled portion 52. Shaft portion 44 suitably terminates at a flat, distal land 70.

With continued reference to FIG. 3 and as discussed in greater detail below in conjunction with FIG. 6, shaft portion 44 suitably comprises one or more grooves 72 extending along the length of shaft portion 44.

Figure 6:
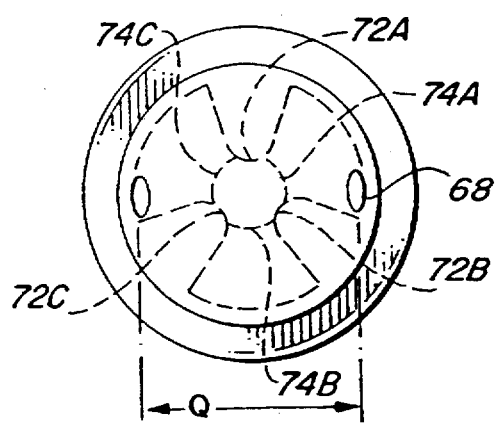
FIG. 6 is an end view of the anchor shown in FIG. 4, taken along line VI—VI of FIG. 4.

More particularly and with reference to FIGS. 3 and 6, respective grooves 72A, 72B, and 72C are suitably spaced apart along shaft 44, forming respective tine sections 74A, 74B, and 74C. As best seen in FIG. 3, each of respective tine sections 74A–74C comprises a portion of respective tine segments 46A–46F. Although respective grooves 72A–72C are substantially semicircular in cross section as shown in FIG. 6, virtually any geometry may be employed such that respective tine sections 74A–74C are spaced apart from one another. In this way, when anchor 40 is installed within a bone mass, bony ingrowth may penetrate the interstices formed by respective grooves 72A–72C intermediate tine segments 74A–74C. The presence of this bony ingrowth helps ensure that anchor 40 remains stationary within the bony mass. In particular, the presence of bony ingrowth within respective grooves 72A–72C substantially impedes rotational migration of anchor 40, as well as substantially impeding axial migration (either into the bone or out of the bone) by enveloping the complex geometric structure comprising shaft 44.

Figure 4:
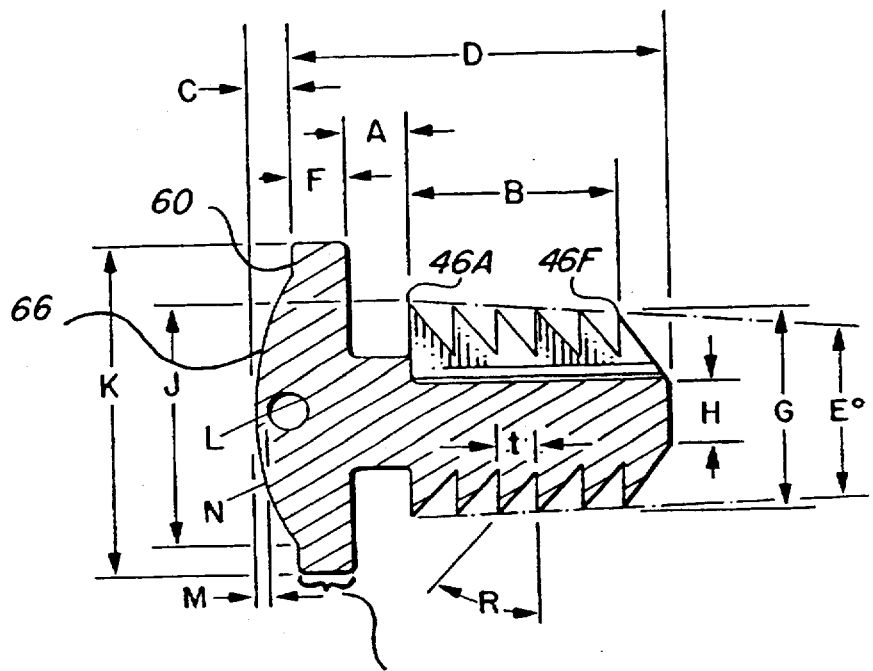
FIG. 4 is a cross-section view of the bone anchor device of FIG. 3 taken along line IV—IV of FIG. 3.
Figure 5:
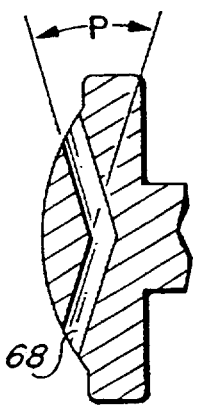
FIG. 5 is a cross-section view of the head portion of the bone anchor device of FIGS. 3 and 4.

Referring now to FIGS. 4–6, the outer diameter of shaft 44 may be substantially constant along its length in accordance with a first embodiment of the invention (not shown). In the alternate preferred embodiment shown in FIG. 4, the outer diameter of the tines suitably decreases, for example linearly, from tine segment 46A to tine segment 46F.

More particularly, the diameter of shaft 44 may decrease along its length approaching land 70, such that an included angle E defined by the convergence of the shaft diameter is suitably on the order of 0–10 degrees or more, and preferably in the range of 5–6 degrees, and most preferably on the order of six degrees. In the illustrated embodiment wherein each respective tine segment 46A–46F is suitably substantially equal in length, i.e., wherein each tine segment has an approximately equal axial dimension, the various angles defined by junction 50 increase from tine segment 46A to tine segment 46F, that is, each respective land 48 corresponding to tine segments 46A–46F decreases along the length of shaft 44 (to the left in FIG. 4), each angled segment 52 also decreases along the length of shaft 44, and the angle defined by junction 50 for each tine segment correspondingly increases along the length of shaft 44 (i.e, from right to left in FIG. 4). In this regard, while the respective angled junctions 50 corresponding to the various tine segments are shown as a sharp corner in the drawing Figures, it may be advantageous from a manufacturing standpoint to include a small radius at junction 50 in lieu of a sharp corner.

With continued reference to FIG. 4, an internal angle R may also be defined for each tine segment. Consistent with the foregoing discussion, the angle R for each tine segment will increase along the length of shaft 44 (i.e., from right to left in FIG. 4).

In a preferred embodiment of the invention, an axial dimension, for example, a common dimension for each respective tine segment 46A–46F, may be defined as shown in FIG. 4. In a particularly preferred embodiment, axial dimension for each tine segment is suitably on the order of 0.025–0.040 inch, and most preferably on the order of about 0.030 inch, such that the length of shaft 44 for the 6 tine embodiment shown in the Figures is on the order of approximately 0.180 inch. In particular, the length of shaft 44 is most desirably approximately 0.120 inch for use in conjunction with small bones or for use with small children, and may suitably be on the order of 0.240 inch for use in middle sized bones or in average sized people, and approximately 0.360 inch for large bones and/or for use in larger individuals.

While any desired angle E may be employed in the context of the present invention, an angle on the order of five degrees facilitates convenient insertion and self-alignment of anchor 40 into bore 28, as discussed in greater detail below.

With continued reference to FIG. 2 and 4–6, a surgeon suitably prepares a reattachment site 21 in the following manner.

With particular reference to FIG. 2B, a bone drill (not shown) is suitably employed to introduce bore 28 in the bone site, which extends through compact layer 22 and cancellous layer 24. The total length of bore 28, i.e., from the outer surface of compact layer 22 until the bottom 29 of bore 28, is referred to in FIG. 2B as dimension 35. With momentary reference to FIG. 4, dimension 35 (FIG. 2B) corresponds to dimension D of anchor 40, and is advantageously in the range of 0.20 inch to 0.50 inch, and most preferably in the range of 0.33 inch to 0.45 inch. In practice, it may be desirable for dimension 35 of bore 28 (FIG. 2B) to exceed dimension D of anchor 40 (FIG. 4) by a small amount, for example on the order of 0.001 to 0.020 inch. In this way, disc portion 43 of head 42 is advantageously disposed beneath the surface of compact bone layer 22 when anchor 40 is installed.

With continued reference to FIG. 2B, a counterbore 30 is suitably created in compact layer 22, either by using the same drill employed to create bore 28 or by using a secondary tool in addition to or in conjunction with the drill used to create bore 28. In order to maintain proper alignment, counterbore 30 and bore 28 are desirably created using a single tool (not shown). With momentary reference to FIGS. 2B, 3, and 4, the axial dimension of counterbore 30 is suitably equal to or slightly greater than the thickness of disc 43 (corresponding to dimension F in FIG. 4), and is suitably on the order of 0.020 to 0.50 inch, and most preferably on the order of about 0.40 inch. The depth of counterbore 30 is limited by the thickness of compact bone layer 22 in the vicinity of the reattachment site, and, hence, the size of anchor 40 is advantageously selected in accordance with the physical dimensions of the reattachment site.

In any event, the depth of bore 28 should be selected so that undersurface 56 of disc 43 engages corresponding surface 31 of counterbore 30; that is, while base 70 of device 40 should desirably be proximate base 29 of bore 28 when anchor 40 is installed, it is not necessary that base 70 of device 40 contact base 29 of bore 28, whereas it is highly desirably that undersurface 56 of device 40 physically engage surface 31 of counterbore 30. In this way, inward axial migration of anchor 40 will be substantially inhibited to the extent the integrity of compact bone layer 22 in the vicinity of counterbore 30 remains intact.

The diameter of bore 28 should be selected to be equal to or slightly smaller than the largest diameter of respective tine segments 46A–46F. More particularly, the diameter of bore 28, illustrated as dimension 32 in FIG. 2B, is advantageously on the order of 0.010 to 0.040 (and most preferably on the order of 0.028 inch) smaller than dimension G (see FIG. 4) of device 40. In this way, the various arcuate junctions 50 corresponding to the tine segments will frictionally engage the circumferential walls of bore 28 during insertion of anchor 40 into device 28. Depending on various physical characteristics of the material comprising anchor 40 as discussed in greater detail below, and further depending on the hardness of the bone and the vicinity of reattachment site 21, and further depending on the physical dimensions of the various tine segments in the vicinity of respective junctions 50, the frictional engagement between shaft 44 and bore 28 may result in a deflection of the tine segments as the device is inserted into the bore, the deflection of compact bone 22 and cancellous bone 24 proximate the device, or a combination of both. To the extent anchor 40 frictionally engages the bone during insertion, the outward flaring of respective tine segments 46A–46F (and particularly in the region of respective arcuate junctions 50) with respect to the bone proximate thereto will inhibit outward axial migration of anchor 40.

Finally, the diameter of counterbore 30 should advantageously be approximately equal to or slightly greater than the diameter of disc 43 (dimension L in FIG. 4). In the preferred exemplary embodiment shown in the drawing Figures, dimension L is suitably on the order of 0.020 to 0.10 inch, and most particularly on the order of 0.040 to 0.075 inch, and most preferably on the order of about 0.0625 inch. Thus, the diameter of counterbore 30 should suitably be on the order of 0.000 to 0.030 inch, and most preferably on the order of 0.020 inch, greater than dimension L to facilitate optimum seating of device 40 within counterbore 30.

With continued reference to FIGS. 2B and 2C, after reattachment site 21 is properly prepared by the surgeon, anchor 40 may be suitably inserted into bore 28, for example by urging the device into the bore by pressure exerted by the surgeon's thumb or forefinger, or by tapping the device with a suitable impact tool. When anchor 40 is firmly seated within the bore, soft tissue 26 may be suitably secured to the attachment site with one or more sutures 36, as is known in the art. In this regard, sutures 36 may be threaded through tunnel 68 prior to inserting anchor 40 into the bore, after the anchor is partially seated within the bore, or upon fully seating the anchor within the bore.

More particularly and with reference to FIGS. 5 and 6, the cross-sectional area of tunnel 68 is suitably large enough to accommodate one or more sutures extending through the tunnel. It is also desirable to ensure that sufficient material is present within dome 66 to avoid breakage even as substantial tension is applied to the sutures, for example during attachment of the soft tissue. Moreover, the cross-sectional area of tunnel 68 should also be sufficient to permit standard suture needles to conveniently pass through the tunnel, even when device 40 is seated within a bone.

To facilitate the convenient threading of sutures through anchor 40 in situ, an included angle P associated with tunnel 68 may be defined, which is suitably on the order of 10–60 degrees, and preferably on the order of 25–35 degrees, and most preferably about 30.6 degrees. Furthermore, the distance between the respective openings comprising tunnel 68 may be conveniently defined as dimension Q (FIG. 6), suitably on the order of 0.030 to 0.090 inch, and preferably on the order of 0.050 to 0.075 inch, and most preferably about 0.060 inch. Finally, the diameter of tunnel 60 is suitably on the order of 0.020 to 0.060 inch, and most preferably about 0.045 inch.

Once anchor 40 is installed within the bone site, for example as shown in FIG. 2C, and soft tissue 26 is suitably reattached to the bone site via sutures 36, it is desirable to minimize irritation of soft tissue 26 and surrounding tissue by device 40. In this regard, it is desirable to seat disc 43 within counterbore 30 to the extent permitted by the anatomical configuration of bone site 21. In addition, it is desirable that the geometry of dome 66 be such as to minimize discomfort associated with the contact between dome 66 and the adjacent anatomy.

More particularly, dome 66 is suitably highly polished, and exhibits a smooth, curved surface, for example a hyperbolic, ellipsoid, or semispherical shape. In addition, the respective openings comprising tunnel 68 may be radiused, bevelled, or otherwise configured to avoid sharp corners. In a particularly conferred embodiment, dome 66 suitably comprises a substantially uniform radius on the order of 0.100 to 0.176 inch, and most preferably on the order of 0.130 inch resulting in a maximum dimension C (FIG. 4) on the order of 0.020 to 0.070 inch, and most preferably about 0.050 inch.

For reattachment sites such as that shown in FIG. 2, i.e., wherein a substantially flat bone surface is available, disc 43 may be substantially seated within counterbore 30. However, it may also be desirable to employ anchor 40 at reattachment sites which are either concave, convex or otherwise irregular. Accordingly, the diameter and thickness of disc 43, as well as various other dimensions of head 42 (in particular the dome 66) may be configured to provide adequate material strength to avoid breakage as tension is applied to the sutures, while at the same time providing smooth, nonabrasive and minimally invasive surfaces to reduce irritation of surrounding tissue.

In accordance with a further aspect of the present invention, anchor device 40 is advantageously made from any suitable biocompatible material, for example titanium alloy, stainless steel, class six implant grade plastic, and the like, or any other biocompatible material which exhibits adequate pullout strength, sufficient strength to avoid breakage as the sutures are pulled, and having sufficiently low brittleness to avoid breakage during long term usage of the device in situ. Alternatively, in view of the relatively short useful life of device 40 (as discussed above), device 40 may be made from a suitable bioabsorbable material, for example, polyglycolic acid, a material distributed by Johnson & Johnson under the name ORTHOSORB™.

In accordance with a further aspect of the invention, shaft 44 and, if desired, neck portion 54 and at least underside 56 of disc 43 may suitable exhibit a course finish to further promote bony ingrowth and thereby further stabilize anchor 40 against any degree of migration.

Figure 7:
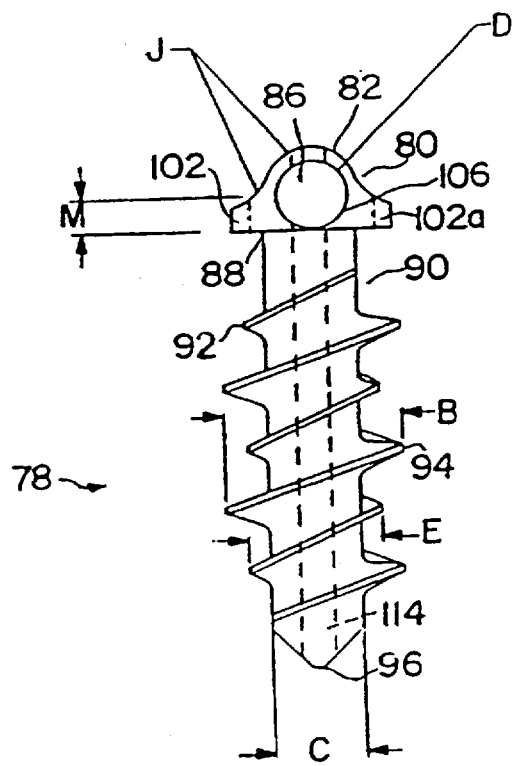
FIG. 7 is a first view of an alternate embodiment of an exemplary anchor.
Figure 8:
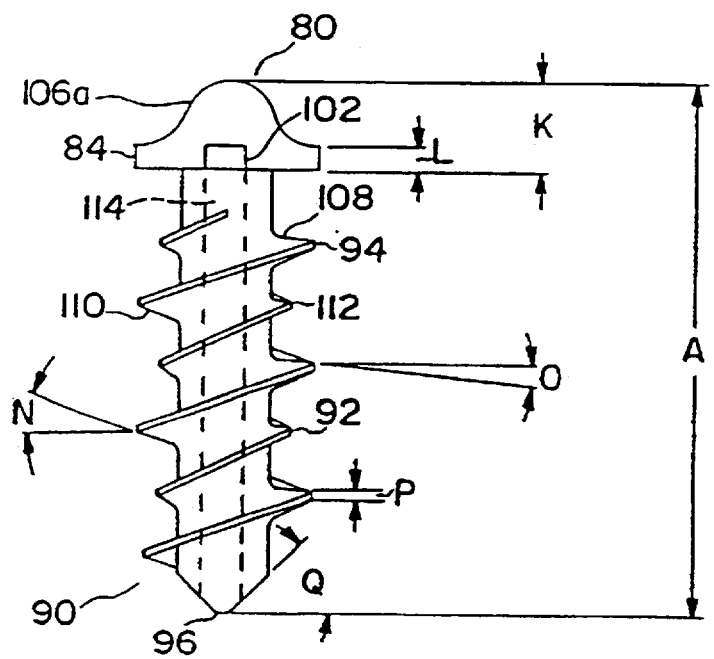
FIG. 8 shows the anchor of FIG. 7 rotated 90 degrees.
Figure 9:
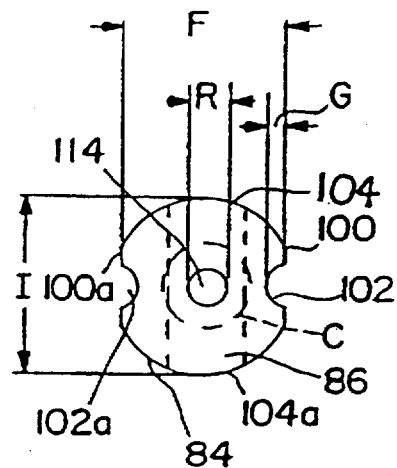
FIG. 9 is a top view of the anchor shown in FIGS. 7 and 8.

In accordance with a further aspect of the present invention, and with reference to FIGS. 7 to 9, the suture anchor 78 suitably comprises a shaft 90 and a head 80. Shaft 90 is suitably integral with head 80, and in a preferred exemplary embodiment, is substantially cylindrical in shape.

With particular reference to FIG. 7, shaft 90 further comprises respective major threads 94 and minor threads 92. As shown, preferably threads 92 and 94 are interleaved and each suitably arranged in a helical pattern. In addition, and with reference to FIG. 8, the distal end 96 of shaft 90 is preferably pointed for easy penetration and self-tapping into the bone matter. Preferably, distal end 96 is formed by tapering or angling of shaft 90, such as at an angle Q on the order of about 30–45 degrees. The outermost point of distal end 96 is preferably rounded, such as by being radiused on the on the order of about 0.010 inch. It should be appreciated, however, that alternative pre-tapping end configurations may be employed in the context of shaft 90 and/or that conventional pre-tapping methodologies (e.g. pre-drilling and the like) may be employed as desired even with self-tapping configurations.

A preferred orientation of interleaved thread patterns 92, 94 is in a so-called "hi-low configuration". As will be appreciated by those skilled in the art, such a configuration includes minor threads having a dimension of between about 60% to about 85%, and most preferably about 75%, of the dimension of the major threads. Such a configuration with bone anchors is believed to offer advantages over other bone screw configurations because it allows for greater recruitment of bone material, and particularly of the soft cancellous bone matter, the part of the bone that the majority of the anchor fastens to. In addition, because only half of the threads have a large diameter, the amount of torque required to set the anchor tends to be reduced.

Referring still to FIG. 7, in a preferred exemplary embodiment of the invention, the spacing between either consecutive major threads 94 or of consecutive minor threads 92 is suitably on the order of 5–16 threads per inch, and most preferably on the order of about 9 threads per inch. Thus, the spacing of the interleaved combination of major and minor threads is suitably between about 10–32 threads per inch, and most suitably on the order of about 18 threads per inch.

In accordance with the preferred exemplary embodiment the diameter of shaft 90, as illustrated by dimension C, is suitably on the order of about 0.040 to about 0.175 inch, and most preferably on the order of about 0.080 or 0.125 inch; the diameter of minor threads 92, as illustrated by dimension E measured from the central axis x of shaft 90 to the outer edge of minor thread 92, is suitably on the order of about 0.060 to about 0.255 inch, and most preferably on the order of about 0.118 to 0.190 inch; and the diameter of major thread 94, as illustrated by dimension B measured from the central axis x of shaft 90 to the outer edge of thread 94, is suitably on the order of about 0.100 to about 0.300 inch, and most preferably on the order of about 0.157 to 0.256 inch.

The particular configuration and dimension of threads 92, 94 may vary depending on a variety of factors. For example, typically it is desirable that the height and number of threads be chosen to optimize pull-out strength and minimize insertion torque as anchor 78 is worked into the bone mass. Preferably, the height of minor thread 92 is between about 25% to about 70% the height of thread 94, and more preferably about 50%.

While anchor 78 is shown as having an equal number of major threads 94 and minor threads 92 per inch, it should be appreciated that the number of threads per inch may vary as between the major and minor thread patterns, or that vary over the length of anchor 78. For example, the number of threads per inch, while being the same for both major threads 94 and minor threads 92 might be suitably varied over the length of anchor 78, say for example with the pitch increasing from bottom 96 to the top of shaft 90. That is, it may be desirable to have more threads per lineal inch in one region along the axis of the shaft than in other regions along the axis of the shaft. It is believed that such a construction may optimize the pull-out strength of anchor 78, while at the same time desirably reducing the stress to the bony material upon insertion of anchor 78.

Threads 92 and 94 are also suitably surface finished to minimize stress on the bony material as anchor 78 is inserted therein. In accordance with a preferred embodiment of this aspect of the present invention, the outer surfaces or edges of threads 92, 94 are optimally rounded or smoothed, for example to exhibit a radiused surface on the order of about 0.002 to about 0.005 inch. As will be appreciated by those skilled in the art, such finish can be engendered through electro-polishing, fine bead sanding or the like.

Referring now to FIG. 8, each of respective threads 92 and 94 preferably comprise an angled helical upper surface 108, an angled helical under surface 110, and a helical edge 112 interconnecting surfaces 108 and 110. Preferably, surface 110 is downwardly angled from the outer edge of threads 92 and 94 to the body of shaft 90. This angle is illustrated by dimension N and, in a preferred embodiment, is typically about 25 degrees. Similarly, upper surface 108 is preferably angled upwardly from the edge of threads 92, 94 to the body of shaft 90, as is illustrated by dimension O, typically about 5 degrees. The thickness P of the helical edge 112 interconnecting upper surface 108 and lower surface 110 is typically about 0.005 inch.

With continued reference to FIG. 7, head 80 suitably comprises a curvalinear dome 82 and a substantially flat, annular undersurface 88 separated by a circumferential segment 84. Head 80 preferably further includes two oppositely facing grooves, e.g., semicircular grooves 102, 102a and a suture tunnel 86, e.g., having a circular or elliptical cross-section, passing through dome 82 such that tunnel 86 extends between grooves 102, 102a. As will be discussed in greater detail below, a driving tool 120 (FIG. 10) suitably adapted to receive head 80 in such way as to minimize the risk of driver slippage when torque is applied to anchor 78 is optimally utilized to set anchor 78 into a bone.

Head 80 is substantially superior to the prior art in that its curvalinear shape minimizes the irritation of surrounding tissue while also minimizing the distance that head 80 protrudes above the bony material. Furthermore, the configuration of head 80 adds additional benefit in that it impedes the migration of anchor 78 into the bone material and makes anchor 78 easily retrievable, a significant advance from the prior art.

Many times, anchors will be inserted so that the entire anchor imbeds below the cortical surface of the bone. After time, the bone will grow over the anchor making it very difficult to retrieve. In this situation, a doctor must bore a hole into the bone and search for the buried anchor. Because head 80 stays in the upper cortical surface of the bone, bony overgrowth will not likely cover head 80 and, thus, head 80 will not likely be lost beneath the cortical surface.

With reference now to FIG. 9, segment 84 preferably is circular in shape suitably exhibiting two substantially flat sides 100, 100a parallel to tunnel 86. Cut or otherwise formed into sides 100, 100a are respective grooves 102, 102a. In a preferred embodiment of this aspect of the invention, the dimension F between sides 100 and 100a is suitably on the order of about 0.060 to about 0.240 inch, and most preferably on the order of about 0.140 inch. The depth G of grooves 102, 102a is suitably on the order of about 0.020 to about 0.080 inch, and most preferably on the order of about 0.050 inch. The radius of grooves 102, 102a is suitably on the order of about 0.020 to about 0.080 inch, and most preferably on the order of 0.050 inch. It should be appreciated however, that grooves 102, 102a may be variously configured such as, for example, exhibiting a square, rectangular or other suitable configuration.

Arc segments 104, 104a of segment 84 are preferably curvalinear, optimally circular in nature. In a preferred exemplary embodiment, dimension I is suitably on the order of about 0.080 to about 0.250 inch, and most preferably on the order of about 0.157 inch.

Referring back to FIG. 7, dome 82 preferably consists of a smooth curved surface, e.g., a symmetrical sinusoidal shaped element having respective connected inward and outward facing arcs. The radii of both arcs are preferably equal and are illustrated as dimension J in FIG. 7. Preferably, dimension J is on the order of about 0.040 to about 0.100 inch, and most preferably on the order of about 0.047 inch.

Preferably dome 82 is configured to possess an upper smooth curvalinear configuration. For example, as shown best in FIG. 8, dome 82 and segment 84 combine to form the structure surrounding tunnel 86, and the distance K from the top of dome 82 to underside 88 is suitably on the order of about 0.060 to about 0.120 inch, and most preferably on the order of 0.080 inch. Preferably, head 80 is suitably dimensioned to ensure that undersurface 88 seats against the outer surface of the bone into which anchor 78 is inserted, while minimizing soft tissue irritation by segment 84; for example, by configuring segment 84 to exhibit a thickness L on the order of about 0.015 to about 0.040 inch, and more preferably on the order of 0.022 inch.

It should be appreciated, however, that other anchor head configurations may be suitably utilized. For example, dome 82 and segment 84 could be suitably modified to maintain the general curvalinear configuration, while at the same time affording other benefits. In this regard, segment 84 could be provided with one or more nibs or other protrusions (not shown) on underside 88 thereof to facilitate attaching of tendons or the like between head 80 of anchor 78 and the bone into which it is inserted.

With reference now to FIGS. 7 and 9, a tunnel 86 is suitably configured to pass completely through head 80 between parallel sides 100 and 100a. Preferably, tunnel 86 exhibits a cross-sectional area sufficiently large enough to permit a standard suture needle to conveniently pass therethrough, particularly in the presence of one or more sutures extending therethrough. Tunnel 86 is a significant advancement over the prior art in that if a suture breaks while in anchor 78, a doctor can conveniently thread a new suture through hole 86. Previously, the anchor had to be removed to insert a new suture. In accordance with a preferred embodiment of this aspect of the present invention, the tunnel 86 exhibits a diameter on the order of about 0.040 to 0.100 inch, and more preferably on the order of about 0.065 inch or 0.075 inch. Tunnel 86 is suitably positioned near underside 88. Preferably, the distance M from an axis passing through the center of tunnel 86 to underside 88 is on the order of about 0.020 to about 0.050 inch, and more preferably on the order of about 0.032 inch.

To minimize discomfort associated with the contact between head 80 and adjacent anatomy, the edges of head 80 and the respective openings comprising tunnel 86 may be radiused, bevelled, or otherwise configured to avoid sharp corners. This can be accomplished by any suitable manner, such as by machining, grinding, electro-polishing, fine bead blasting and the like. In particular, respective junctions 106 and 106a of tunnel 86 (i.e., the tunnel openings) are preferably radiused to prevent sutures passed through tunnel 86 from being snagged or severed by any sharp corners contained thereon. In a preferred embodiment of the invention, the radius of edges 106, 106a is suitably on the order of about 0.004 inch.

Anchor 78 may be configured to exhibit any length A depending on the nature and type of bone it is intended to be used with. In accordance with a preferred aspect of the present invention, anchor 78 exhibits a length on the order of about 0.125–1.5 inch, and most preferably on the order of 0.472–0.551 inch.

Still referring to FIGS. 7 to 9, in a further embodiment of the present invention anchor 78 may be suitably configured with an axial bore 114 extending through the entirety thereof. Bore 114 preferably exhibits a diameter R suitably on the order of about 0.020 to about 0.10 inch, and more preferably on the order of about 0.030 to about 0.075 inch. In general, preferably the thickness of the walls of shaft 90 surrounding bore 114 are on the range of about 0.020 to about 0.10, more preferably about 0.025 inch.

Anchor 78 having bore 114 extending therethrough is, in accordance with this aspect of the present invention, suitably configured to enable a guide wire to be advantageously passed through anchor 78 while in use. For example, in some circumstances, it may be desirable to pin soft tissue to a bone before inserting a bone anchor. For example, if a doctor is fixing a tendon in a shoulder, he may want to pin the tendon in place before inserting the anchor. In this respect, once the tendon is lightly secured in place, the doctor may install a suitable guide wire into a desired position and slide anchor 78 with bore 114 over the wire for anchor position guidance. In this situation, when anchor 78 is inserted into the bone matter, head 80 advantageously will reside directly on top of the soft tissue, securing the tissue between underface 88 and the bone surface, thereby adding extra stability to the tissue/bone interface.

Because, in this configuration, head 80 operatively engages the soft tissue, to aid in holding the tissue to the bone, a preferred embodiment of head 80 may include small teeth (nibs) on underside 88, or, alternatively, underside 88 may be concave in shape instead of substantially flat. In addition to the configuration of head 80 in accordance with this aspect, a doctor can also utilize sutures passed through tunnel 86 of head 80 to further secure the soft tissue in place.

Figure 12:
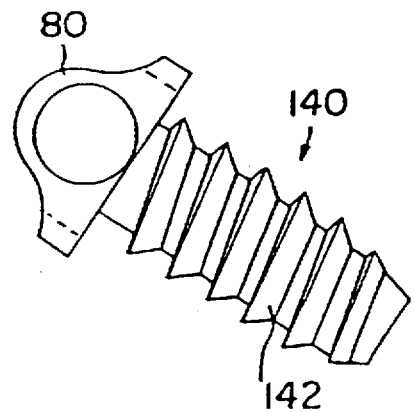
FIG. 12 is an alternate thread configuration useful in the subject anchors.

In accordance with a further aspect of the invention, as shown in FIG. 12, any suitable head configuration, e.g., domed head 80, as described above, can be used in conjunction with "pushtite" threads 142 which comprise a suitable helical screw thread pattern. Threads 142 are configured such that anchor 140 can be secured in the bone by pushing it into a pre-tapped hole, and can be removed by unscrewing it. The preferred embodiment of anchor 140 differs from the tine configuration of anchor 40 in that anchor 140 can be advantageously backed out of the bone, while retaining the deflecting properties of the tines discussed above in conjunction with FIGS. 3–6. Anchor 40, once inserted, tends to be difficult to remove because tines tend to catch. With the embodiment shown in FIGS. 7–9 and in FIG. 12, to remove anchor 140, driving tool 120 (FIG. 10) can be used in conjunction with head 80 to reverse it out.

Figure 13:
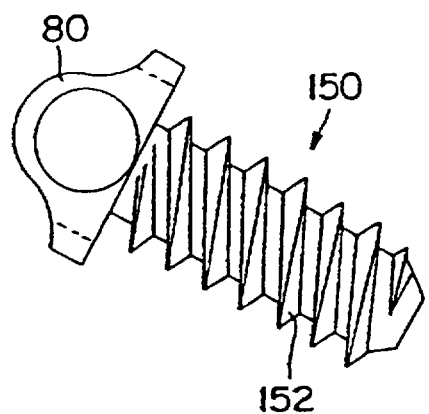
FIG. 13 is a further alternate thread configuration using in accordance with the present invention.

In accordance with yet a further aspect of the invention, as shown in FIG. 13, a suitable head (e.g., head 80) can be used in conjunction with "twin lead" threads 152 which comprise a plurality of equal height interleaved helices. A benefit of anchor 150 is that it can be secured into a pre-tapped hole in two revolutions, yet still provide an acceptable pull-out strength that is similar to other threaded anchors.

Figure 10:
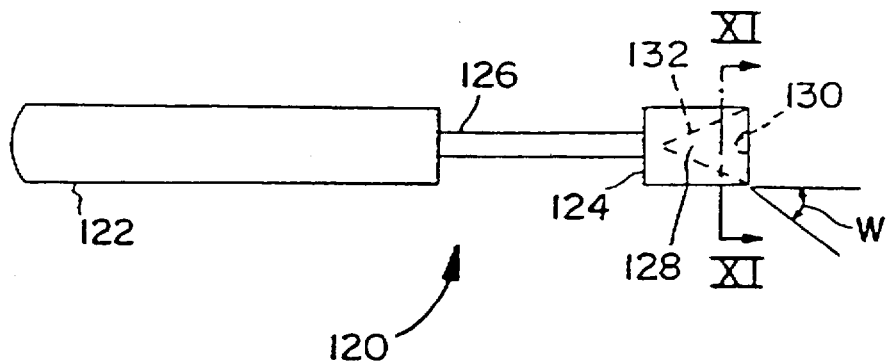
FIG. 10 is a side elevation view of an exemplary embodiment of a driving tool in accordance with the present invention.
Figure 11:
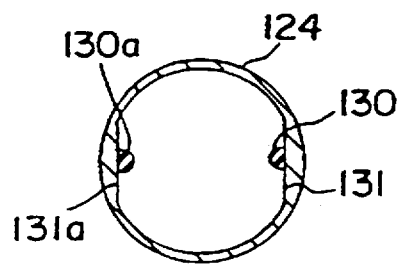
FIG. 11 is a cross-section view of the driving head shown in FIG. 10 taken along lines XI—XI of FIG. 10.

Referring now to FIGS. 10 and 11, driving tool 120 suitably comprises a handle 122, a driving head 124, and a shaft 126 interposed therebetween. Driving head 124 is positioned at the distal end of shaft 126 and preferably comprises a hollow cylindrical cavity 128. Respective oppositely displaced tabs 130 and 130a are suitably provided on the inside of cavity 128. Driving head 124 is suitably configured to fit over and/or engage head 80 of anchor 78 (see FIGS. 7 to 9) with tabs 130 and 130a positioned to fit within grooves (notches) 102 and 102a in head 80. In accordance with a preferred aspect of the invention, driving head 124 may exhibit a depth sufficient to receive the entirety of head 80 within. Typically the depth of driving head 124 will be slightly larger than the height of head 80, and is suitably on the order of 0.065–0.125, and most preferably on the order of about 0.085 inch.

A further aspect of driving head 124 is that the inside wall 132 of cylindrical cavity 128 is tapered inward such that when head 80 is inserted into driving head 124, head 80 wedges against inside wall 132, thus creating an interference or friction fit and securing head 80 inside driving head 124. In addition, because head 80 is held inside cavity 128 by an interference or friction fit, head 80 will release from cylindrical cavity 128 when pressure is reduced between the head and the inside wall (i.e., when the driving tool is pulled away from the anchor). The taper of inside wall 132 is shown by dimension W and may vary depending on the dimensions of head 80; however, dimension W is generally on the order of about 5 degrees.

Because of this unique configuration, when anchor 78 is inserted into driving tool 120, it will not fall out, allowing a doctor to strategically place the anchor in hard to reach places without needing to hold the anchor with his other hand. In addition, this configuration can make surgery safer and more efficient because it reduces the chances of dropping the anchor inside the body.

Although the subject invention has been described herein in conjunction with the appended drawing Figures, those skilled in the art will appreciate that the scope of the invention is not so limited. Various modifications in the arrangement of the components discussed and the steps described herein for using the subject device, may be made without departing from the spirit and scope of the invention as set forth in the appended claims.

We claim:

1. A screw type bone anchor for attaching soft tissue to a bone, comprising:
    a head having a central dome with a suture bore extending through the dome and a pair of substantially flat, oppositely disposed lands configured about said dome, said lands being configured for engagement by a driving tool for inserting said anchor into the bones; and
    a shaft extending from said head, said shaft including a first series of helical threads having a first diameter, and a second series of helical threads interleaved with said first series of threads, said second series of helical threads being characterized by a second diameter substantially different than said first diameter.

2. The anchor of claim 1, wherein said suture bores configure to accommodate a plurality of sutures.

3. The anchor of claim 1, wherein each of said lands further comprises a groove configured to receive a corresponding tab of a driving tool.

4. The anchor of claim 1, further comprising an axial guide wire bore extending along the length of said anchor, such that a guide wire may be journaled through said guide wire bore.

* * * * *